United States Patent
Chace et al.

(10) Patent No.: US 9,551,696 B2
(45) Date of Patent: Jan. 24, 2017

(54) CLEANABILITY ASSESSMENT OF SUBLIMATE FROM LITHOGRAPHY MATERIALS

(71) Applicant: GLOBALFOUNDRIES INC., Grand Cayman (KY)

(72) Inventors: Mark S. Chace, Beacon, NY (US); Martin Glodde, Mahwah, NJ (US); Margaret C. Lawson, Lagrangeville, NY (US); Janine L. Protzman, Poughkeepsie, NY (US); Qin Yuan, Poughquag, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 283 days.

(21) Appl. No.: 14/311,380

(22) Filed: Jun. 23, 2014

(65) Prior Publication Data
US 2015/0369789 A1    Dec. 24, 2015

(51) Int. Cl.
*B08B 7/04* (2006.01)
*G01N 21/00* (2006.01)
*G03F 7/42* (2006.01)
*G01N 33/44* (2006.01)
*G03F 7/20* (2006.01)
*B08B 7/00* (2006.01)

(52) U.S. Cl.
CPC ............ *G01N 33/44* (2013.01); *B08B 7/00* (2013.01); *B08B 7/0035* (2013.01); *B08B 7/04* (2013.01); *G03F 7/70916* (2013.01)

(58) Field of Classification Search
CPC ............ B08B 7/00; B08B 7/04; B08B 7/071; B08B 7/0064; B08B 7/0014; B08B 7/0035; B08B 7/0057; G01N 1/2202; G01N 2001/028; G01N 2001/2282; G01N 2001/4033; G03F 7/70916
See application file for complete search history.

(56) References Cited

U.S. PATENT DOCUMENTS

| | | | |
|---|---|---|---|
| 6,125,687 A | 10/2000 | McClelland et al. | |
| 6,144,029 A | 11/2000 | Adler | |
| 6,426,168 B1 | 7/2002 | Johnson | |
| 6,495,825 B1 | 12/2002 | Chace et al. | |

(Continued)

OTHER PUBLICATIONS

ASTM, "Standard Test Method for Total Mass Loss and Collected Volatile Condensable Materials from Outgassing in a Vacuum Environment", Annual Book of ASTM Standards, 1993, p. 1-8, E 595-93.

(Continued)

*Primary Examiner* — Saeed T Chaudhry
(74) *Attorney, Agent, or Firm* — Yuanmin Cai; Hoffman Warnick, LLC

(57) ABSTRACT

A method of testing the cleanability of polymerized sublimate outgassed from a lithography material during a thermal heating process including; placing a wafer on a wafer hotplate inside a chamber with the wafer being covered by a lithography material; placing a target, having a starting composition, above the wafer in the chamber; heating the wafer using the wafer hotplate in an attempt to outgas a sublimate, where the sublimate condenses on the target; forming a polymerized sublimate on the target; and applying organic solvents to the target to determine the cleanability of the polymerized sublimate.

20 Claims, 6 Drawing Sheets

(56) References Cited

U.S. PATENT DOCUMENTS

| 7,070,832 B2 * | 7/2006 | Goldstein ............. B08B 7/0092 |
| | | 427/154 |
| 7,078,709 B2 | 7/2006 | Herbst et al. |
| 7,089,812 B2 | 8/2006 | Månsson et al. |
| 2002/0030801 A1 | 3/2002 | Endo et al. |
| 2008/0248208 A1 | 10/2008 | Chace et al. |

OTHER PUBLICATIONS

Hien et al, "Photoresist Outgassing at 157 nm Exposure", Advances in Resist Technology and Processing XVIII, 2001, p. 439-447, Proceedings of SPIE vol. 4345.

Kunz et al, "Outgassing of organic vapors from 193 nm photoresists: Impact on atmospheric purity near the lens optics", Journal of Vacuum Science and Technology B, 1999, p. 3330-3334, vol. 17 No. 6.

Maxim et al, "Quantitative measurement of resist outgassing during exposure", Advances in Resist Materials and Processing Technology XXVI, 2009, Proceedings of SPIE vol. 7273, 72733Z.

* cited by examiner

CLEANABILITY ASSESSMENT OF SUBLIMATE FROM LITHOGRAPHY MATERIALS

BACKGROUND

The present invention relates to the field of characterizing condensable compounds outgassed from organic films during heating; more specifically, an apparatus and a method for characterizing the cleanability of polymerized sublimate.

In the field of semiconductor manufacturing, lithography thermal heating processes may be used to cure organic films. The lithography process may include UV lithography, extreme UV (EUV) lithography, and electron-beam (e-beam) lithography. All organic materials used in lithography processes (such as photoresists, optical planarization materials, and anti-reflective coatings) outgas condensable compounds during post-apply bake and other thermal processes. The condensable compounds can subsequently condense on processing equipment surfaces.

SUMMARY

According to one embodiment of the present invention, a method of testing the cleanability of condensate generated during thermal processing of lithography materials is provided. The method may include placing a wafer on a wafer hotplate inside a chamber with the wafer being covered by a lithography material; placing a target in the chamber above the wafer, wherein the target has a starting composition on a target surface thereof; heating the wafer using a thermal heating process, wherein the lithography material outgases a sublimate that condenses on the target surface forming a condensation composition; heating the target using a target hotplate forming a polymerization composition, the polymerization composition having a polymerized sublimate; applying organic solvents to the target causing a final target surface on the target, the final target surface having a post-cleaning composition; and comparing the post-cleaning composition to the starting composition to determine a cleanability of the polymerized sublimate.

According to another embodiment of the present invention, a method of testing the cleanability of condensate generated during thermal processing of lithography materials is provided. The method may include placing a wafer on a wafer hotplate inside a chamber with the wafer being covered by a lithography material; placing a target in the chamber above the wafer, wherein the target has a starting composition on a target surface thereof; heating the wafer using a thermal heating process, wherein the lithography material outgases a sublimate that forms a test composition on the target surface; applying an organic solvent to the target causing a final target surface on the target, the final target surface having a post-cleaning composition; and comparing the post-cleaning composition to the starting composition to determine a cleanability of the lithography material.

According to another embodiment of the present invention, a method of testing the cleanability of condensate generated during thermal processing of lithography materials is provided. The method may include placing a target in a chamber; heating a material in the chamber causing a sublimate to outgas from the material; heating the target forming a polymer composition, wherein the polymer composition includes a polymerized sublimate; and analyzing the polymer composition for crosslinking.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
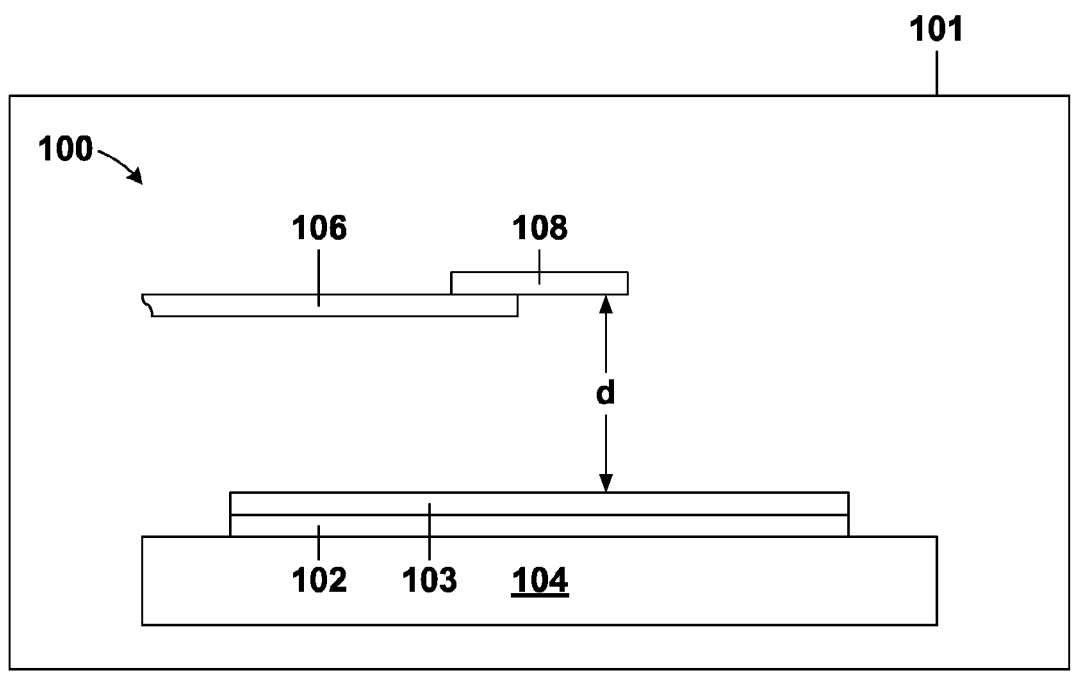
FIG. 1 is a cross section view of an apparatus according to an exemplary embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the disclosed structures and methods, as oriented in the drawing figures. The terms "overlying", "atop", "on top", "positioned on" or "positioned atop" mean that a first element, such as a first structure, is present on a second element, such as a second structure, wherein intervening elements, such as an interface structure may be present between the first element and the second element. The term "direct contact" means that a first element, such as a first structure, and a second element, such as a second structure, are connected without any intermediary conducting, insulating or semiconductor layers at the interface of the two elements.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is rather focused on the distinctive features or elements of various embodiments of the present invention.

The present invention relates to the field of characterizing condensable compounds outgassed from organic films during heating; more specifically, an apparatus and a method for characterizing the cleanability of polymerized sublimate. Ideally, it may be desirable to test the cleanability of polymerized sublimate outgassed from a lithography material before mass production. One way to test the cleanability of polymerized sublimate outgassed from a lithography material may include a wafer having a lithography material, heating the wafer to produce a sublimate, forming a condensed sublimate on a target, heating the target forming a polymerized sublimate, and analyzing the cleanability of the polymerized sublimate.

It should be noted that the term "condense" may be the phase change of condensation or deposition, and a condensed sublimate may be a liquid or a solid. Additionally, it should be noted that the chamber being used to test cleanability may simulate a representative chamber, where the representative chamber is any chamber used during production, fabrication, or any other heating process.

FIG. 1 is a demonstrative illustration of an apparatus 100 during an intermediate step of a method of testing the cleanability of polymerized sublimate outgassed from a lithography material. More specifically, the method can start with the apparatus 100 in a chamber 101. The apparatus 100 may include a wafer 102 on a wafer hotplate 104 and a target 108 above the wafer 102. It should be noted that each step may be conducted in the chamber 101, a different chamber, or any variation therein.

The wafer 102 may be placed in the chamber 101. A lithography material 103 may be directly on the wafer 102. The lithography material 103 may include a mid-UV (ultraviolet) photoresist, either positive or negative, a deep-UV (DUV) photoresist, either positive or negative, or other similar materials such as optical planarization materials (OPL) or anti-reflective coatings (ARC). The wafer 102 may be any material known in the art, such as, for example, silicon. The wafer 102 may be positioned directly on the wafer hotplate 104. The wafer hotplate 104 may be any surface capable of heating the wafer 102 and may simulate a post-apply bake process or other thermal heating processes.

The target 108 may be generally positioned a distance (d) above the wafer 102 and the lithography material 103. The distance (d) may range from 1 cm to 5 cm. The target 108 may be any material known in the art and may be chosen to simulate a possible material present in the chamber or any other material on which the sublimate may condense. In an embodiment, the target 108 may be a quartz disk. It should be noted that the term "condense" may be the phase change of condensation or deposition, and a condensed sublimate may be a liquid or a solid. The target 108 may be analyzed for a starting composition, on a target surface, to create a composition baseline for comparison, also known as zeroing the measurement. The target 108 may be temperature controlled to simulate a surface in the chamber. The target 108 may be temperature controlled relative to the ambient chamber temperature or the temperature of the wafer 102 or any other material within the chamber. Temperatures of the target 108 ranging from 20° C. to 35° C. may be desirable to promote condensation.

The target 108 may be held by a target holder 106. The target holder 106 may hold or support the target 108 in a desired location within the chamber 101, where the desired location may be the distance (d) above the wafer 102 and the lithography material 103. The target holder 106 may be any material known in the art, including, but not limited to, stainless steel, aluminum, and ceramics. The target holder 106 may be the means to control the temperature of the target 108, by conduction, convection, or any other means.

Figure 2:
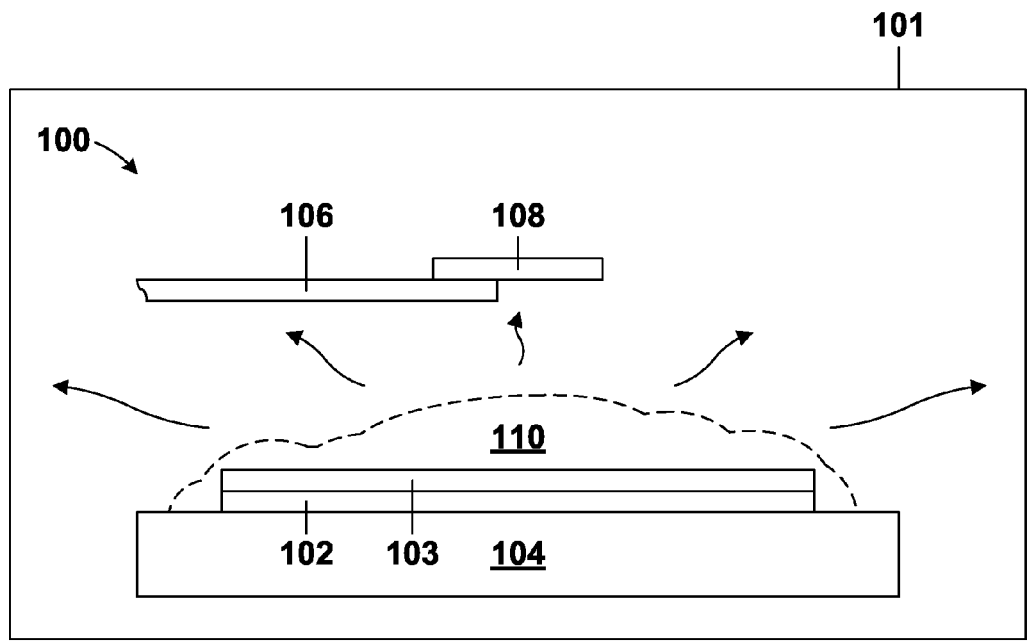
FIG. 2 is a cross section view of the apparatus and illustrates a heating process of a wafer having a lithography material that outgases a sublimate.
Figure 3:
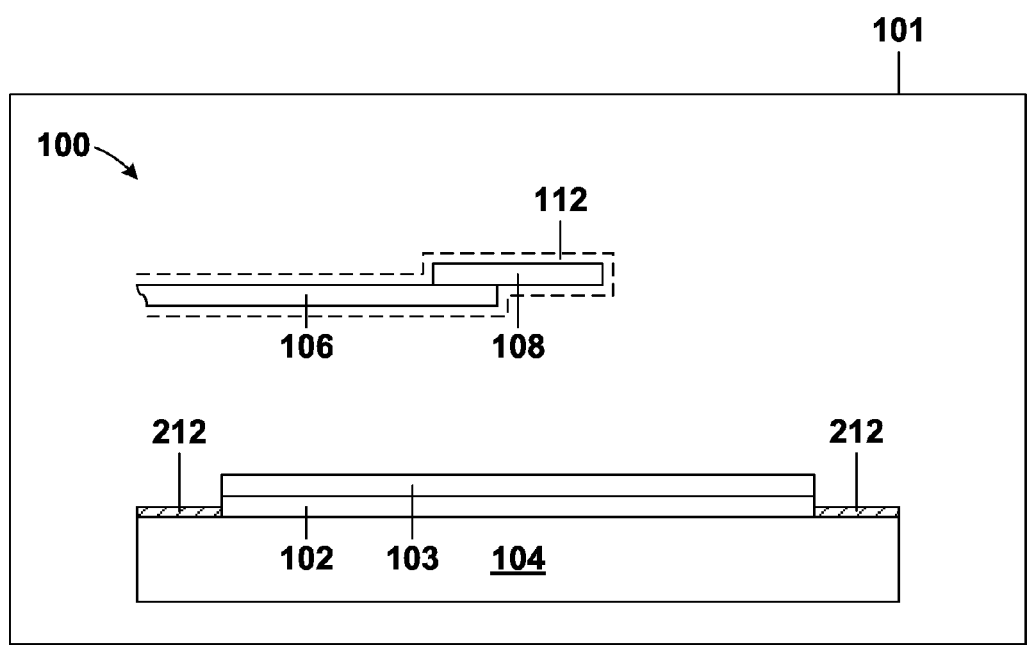
FIG. 3 is a cross section view of the apparatus and illustrates condensation of the sublimate on a target.

FIGS. 2 and 3 are demonstrative illustrations of the apparatus 100 during an intermediate step of a method of testing the cleanability of polymerized sublimate outgassed from the lithography material 103. More specifically, the method may include heating the wafer 102 on the wafer hotplate 104.

In a typical lithography process a lithography material may be formed on a wafer and a thermal heating process, such as a post-apply bake process, may be used to cure the lithography material. The post-apply bake process may typically occur at temperatures ranging from 50° C. to 400° C. The heating time of a typical post-apply bake process may range from approximately 30 s to 120 s. The post-apply bake process may cause the lithography material to outgas a sublimate that may condense on chamber surfaces. The sublimate may include monomers capable of polymerization or crosslinking.

In addition, a sublimate that polymerizes and crosslinks on hot surfaces may be very difficult to clean, if not impossible. Conversely, a sublimate that does not polymerize or crosslink may be relatively easy to clean or remove using known techniques. It may be important to know what lithography materials may outgas a non-cleanable sublimate.

Relating to the present embodiment, the wafer hotplate 104 may function as a heat source and may be in direct contact with the wafer 102 to allow for efficient heat transfer. The wafer 102 and the lithography material 103 may be heated to simulate the thermal heating process described above. The thermal heating process may cause the lithography material 103 to outgas a sublimate 110, which may move freely in the chamber 101. The sublimate 110 may be a mixture of chemicals, including monomers, which may sublime from the lithography material 103. The sublimate 110 may condense on any exposed surface in the chamber 101 forming a condensed sublimate 112, where the condensed sublimate 112 may be a solid or liquid form of the sublimate 110. The sublimate 110 may possibly condense and polymerize on hot surfaces and may form a polymerized sublimate 212. The hot surfaces may include any hot surfaces in the chamber 101, including hot processing surfaces and hot wafer surfaces. The hot wafer surface may be any surface of the wafer 102 or the lithography material 103. The hot processing surface may be any other surface within the chamber.

The polymerized sublimate 212 may also crosslink. Crosslinking of the polymerized sublimate 212 may be undesirable because the polymerized sublimate 212 may be uncleanable. It may be relatively easy to clean the condensed sublimate 112 and relatively hard to clean the polymerized sublimate 212. In an embodiment, the condensed sublimate 112 may condense on the target 108. It may be desirable to control the temperature of the target 108 to promote condensation rather than immediate polymerization or crosslinking to increase the sample size of the polymerized sublimate 212.

Figure 4:
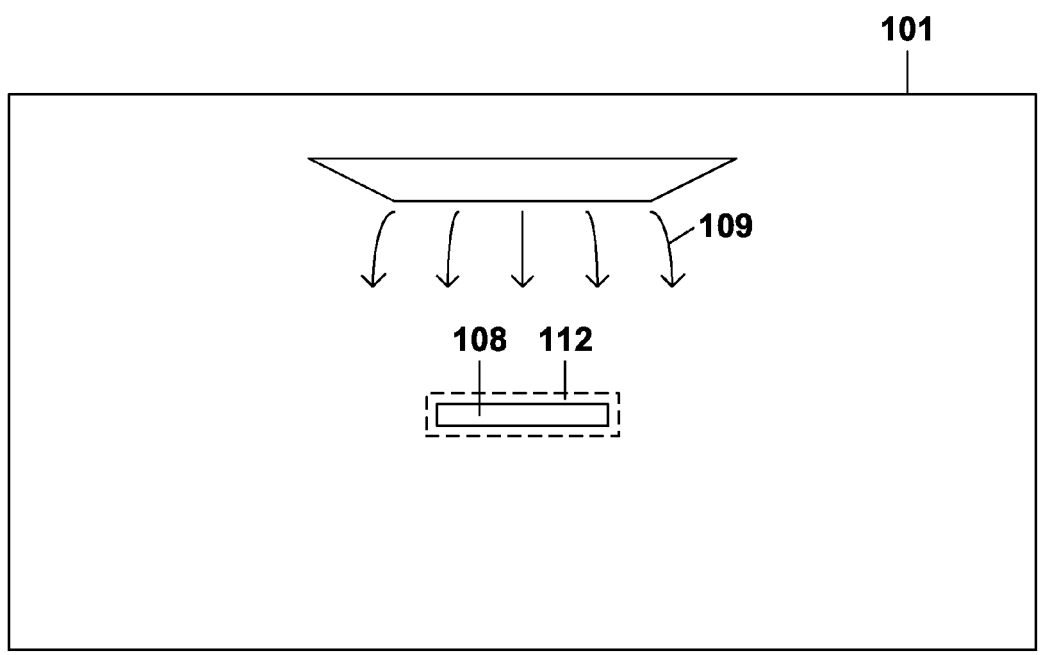
FIG. 4 illustrates the determination of a condensed sublimate present on the target.

FIG. 4 is a demonstrative illustration of the target 108 during an intermediate step of a method of testing the cleanability of polymerized sublimate 212 outgassed from the lithography material 103. More specifically, the method may include analyzing the target 108 for a condensation composition on the target surface.

The condensation composition may include the composition of the condensed sublimate 112. The target 108 may be analyzed for the presence of the condensation composition using a composition analysis 109, such as, for example, ultraviolet-visible spectroscopy (UV-Vis), Fourier transformation infrared spectroscopy (FTIR), or other analysis techniques. UV-Vis and FTIR are non-destructive and may be performed without damaging the target 108 or altering the condensation composition present on the target 108. The condensation composition may be compared to the starting composition to possibly determine whether the lithography material 103 did outgas the sublimate 110, or to determine the amount of sublimate 110 outgassed. The process may stop here if the difference between the starting composition and the condensation composition is negligible.

Figure 5:
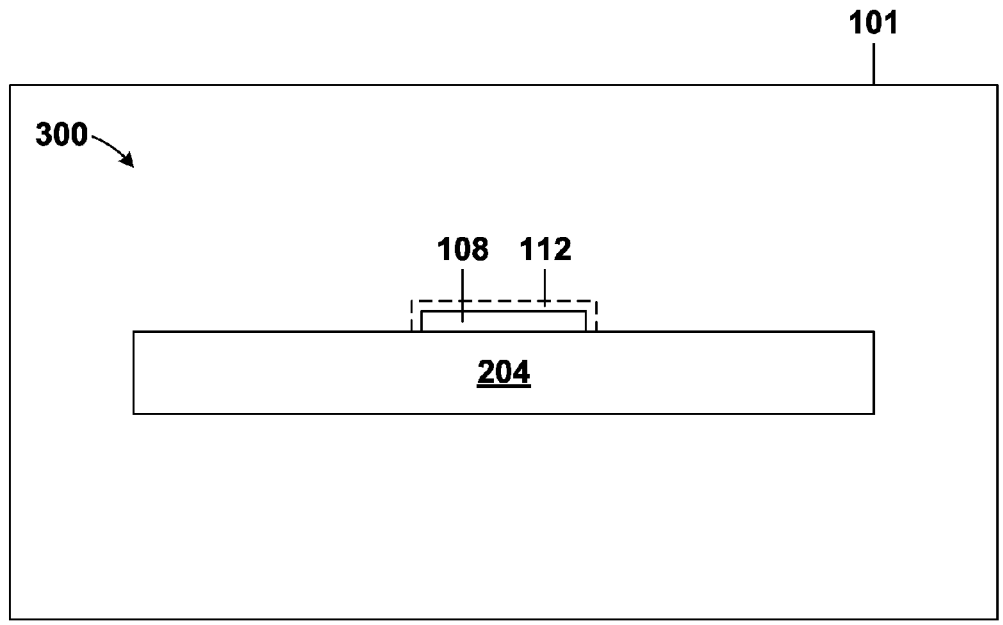
FIG. 5 is a cross section view of another apparatus and illustrates the heating of the target using a target hotplate.

FIG. 5 is a demonstrative illustration of an apparatus 300 during an intermediate step of a method of testing the cleanability of polymerized sublimate 212 outgassed from the lithography material 103. More specifically, the method may include heating the target 108 on a target hotplate 204.

The target 108 may be placed on a target hotplate 204. The target hotplate 204 may be a different hotplate from the wafer hotplate 104 to avoid possible contamination. The target hotplate 204 may function as a heat source and may be in direct contact with the target 108 to allow for efficient heat transfer. The target 108 may be heated to temperatures ranging from 50° C. to 400° C. to simulate hot surfaces in the chamber 101 before, during, or after heating of the wafer 102. The target 108 may be heated for a time range from 5 min to 120 min. The condensed sublimate 112 may form the polymerized sublimate 212 and may crosslink.

Figure 6:
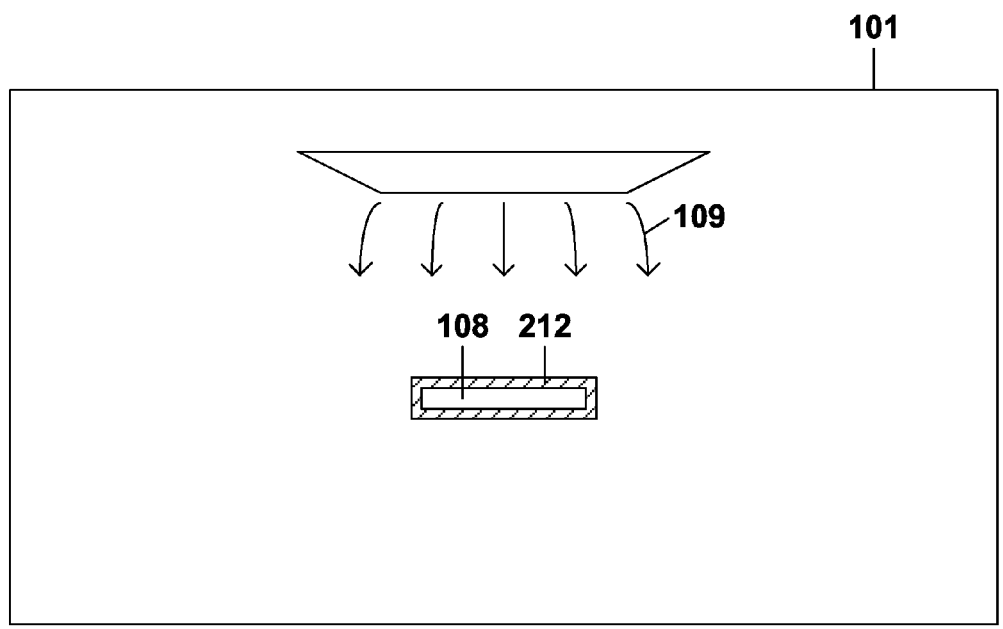
FIG. 6 illustrates the analysis of the target for a polymerization composition.

FIG. 6 is a demonstrative illustration of the target 108 during an intermediate step of a method of testing the cleanability of polymerized sublimate 212 outgassed from the lithography material 103. More specifically, the method may include analyzing the target 108 for a polymer composition on the target surface. The polymer composition may include the polymerized sublimate 212, where the polymerized sublimate 212 may be representative of sublimate that has polymerized on hot surfaces in the chamber during the heating of the wafer 102. The target 108 may be analyzed using the composition analysis 109 described above.

Figure 7:
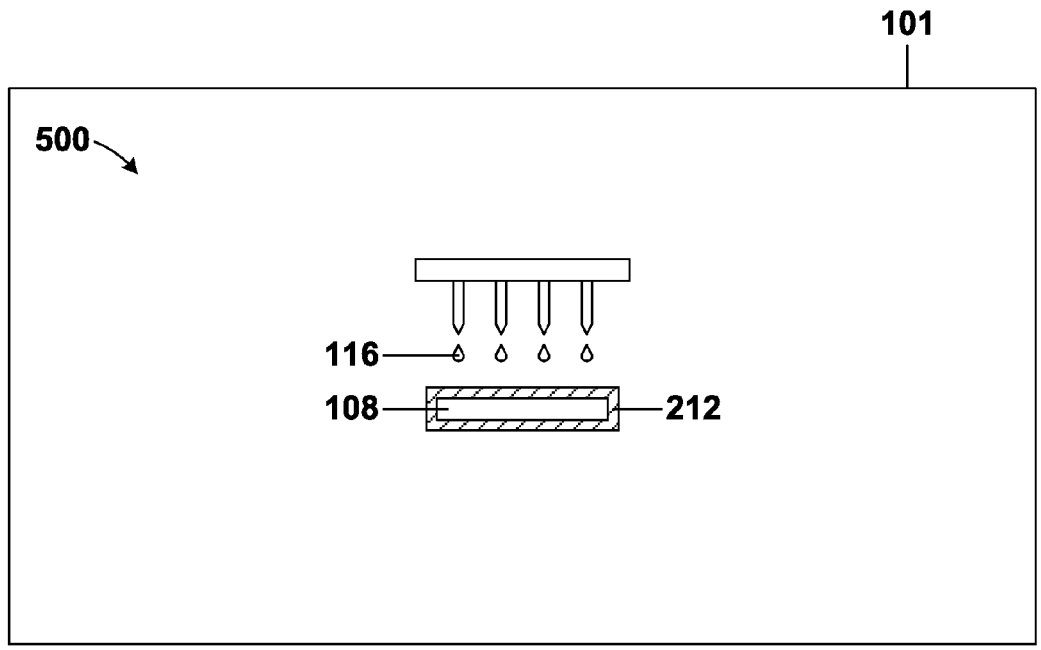
FIG. 7 is a cross section view of another apparatus and illustrates the application of organic solvents to the target.

FIG. 7 is a demonstrative illustration of an apparatus 500 during an intermediate step of a method of testing the cleanability of polymerized sublimate 212 outgassed from the lithography material 103. More specifically, various organic solvents 116, such as acetone, ethanol, isopropanol, hexanes, and ether, may be applied to the target 108 in an attempt to clean the polymerized sublimate 212 from the target 108.

Figure 8:
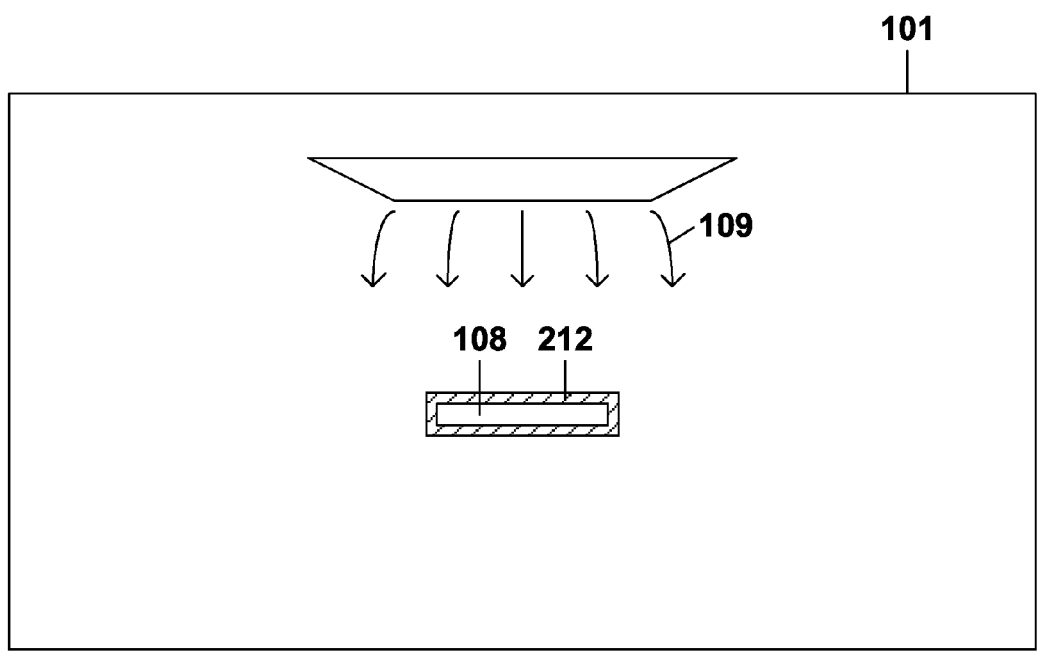
FIG. 8 illustrates the analysis of the target for cleanability after application of the organic solvents.

FIG. 8 is a demonstrative illustration of the target 108 during a possible final step of a method of testing the cleanability of polymerized sublimate 212 outgassed from the lithography material 103. More specifically, the target 108 may be analyzed using the composition analysis 109, described above, to determine a post-cleaning composition on the target surface.

If the polymerized sublimate 212 crosslinked, the post-cleaning composition may include the polymerized sublimate 212 or a residual portion of the polymerized sublimate 212. The post-cleaning composition may be compared to the starting composition to determine the cleanability of the polymerized sublimate 212. If the post-cleaning composition is equal to, or substantially similar to, the starting composition, the lithography material 103 may be considered cleanable and may be allowable or desirable for fabrication. If the post-cleaning composition is not substantially similar to the starting composition, the lithography material 103 may be considered undesirable for fabrication. The post-cleaning composition may also be compared to the polymer composition and the starting composition to determine a range of cleanability.

Figure 9:
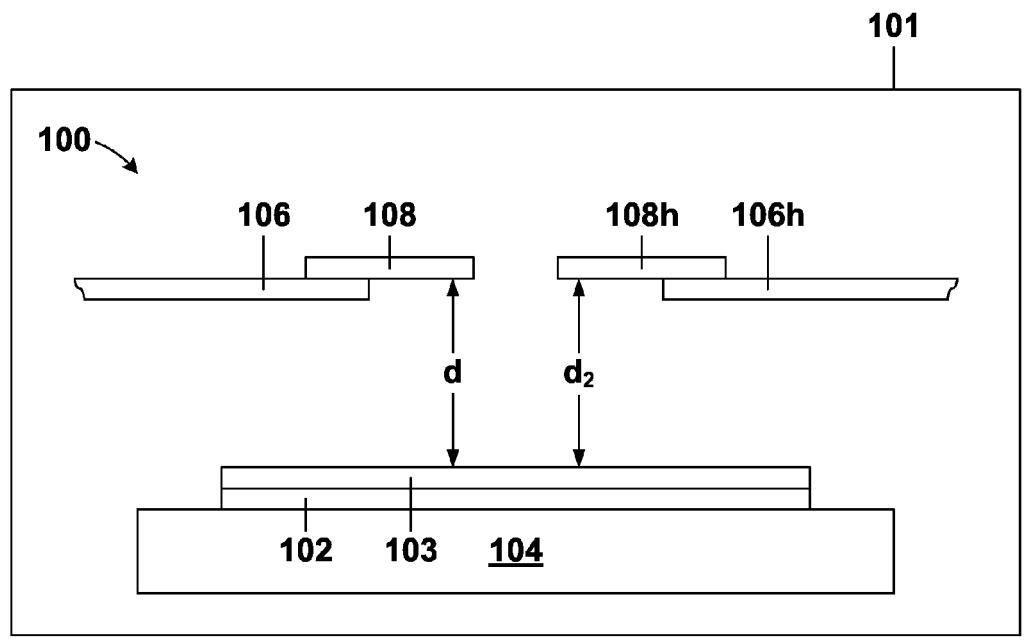
FIG. 9 is a cross section view of an alternative apparatus and illustrates the presence of the target and a hot target in the chamber.
Figure 10:
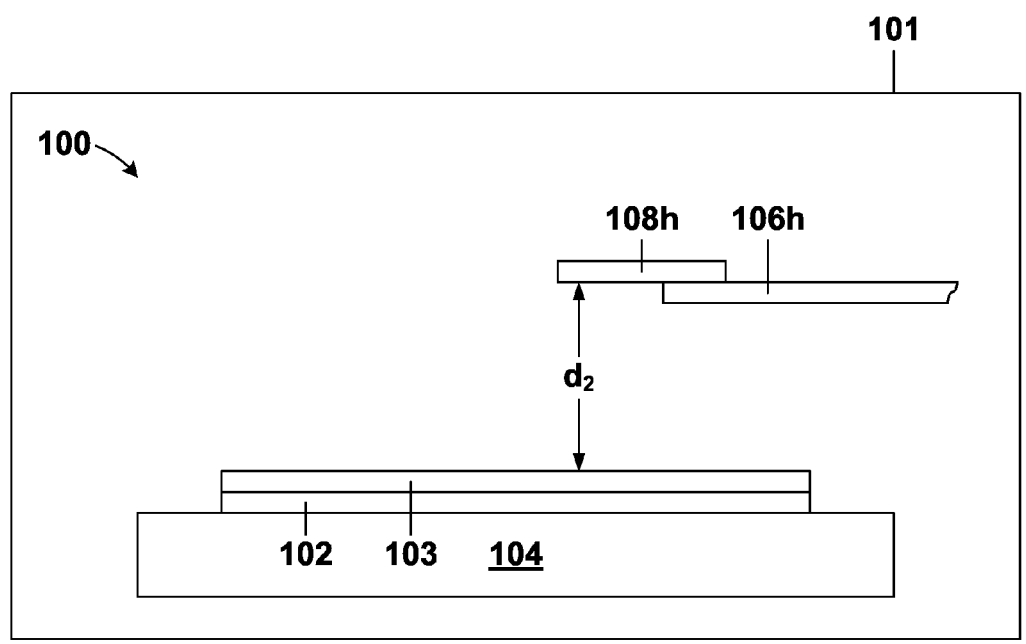
FIG. 10 is a cross section view of an alternative apparatus and illustrates the presence of only the hot target in the chamber.

FIGS. 9 and 10 are demonstrative illustrations of an alternative embodiment of the apparatus 100. More specifically, a hot target 108h may be held by a hot target holder 106h may be present in the chamber 101 during the heating of the wafer 102.

The target 108 may be cold or cool to promote condensation as described in the exemplary embodiment illustrated in FIGS. 1-8. A lower temperature may be desirable for the target 108 to promote condensation rather than immediate polymerization to increase a final amount of polymerization, as described above. However, it is possible to use a hot target 108h to cause polymerization without the need to form the condensed sublimate 112 on the target 108, as described above in reference to FIG. 3; and without the need to heat the target 108 to form the polymerized sublimate 212, as described above in reference to FIG. 5. One alternative embodiment may include the target 108 and the hot target 108h during the heating of the wafer 102 where the target 108 may be the distance (d) from the wafer 102 and the lithography material 103, as described above. The hot target 108h may be a second distance ($d_2$) from the wafer 102 and the lithography material 103. The second distance ($d_2$) may be the same as the distance (d). Another alternative embodiment may not include the target 108 but may include the hot target 108h, where the hot target 108h may be the second distance ($d_2$) from the wafer 102 and the lithography material 103. The hot target 108h may also be cleaned by the organic solvents 116 similarly to the target 108 described in reference to FIG. 7. The hot target 108h may then be analyzed to determine a hot post-cleaning composition similar to the post-cleaning composition of the target 108 described in reference to FIG. 8. The hot post-cleaning composition may be compared to a hot starting composition to determine the cleanability.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method comprising:
   placing a wafer on a wafer hotplate inside a chamber with the wafer being covered by a lithography material;
   placing a target in the chamber above the wafer, wherein the target has a starting composition on a target surface thereof;
   heating the wafer using a thermal heating process, wherein the lithography material outgases a sublimate that condenses on the target surface forming a condensation composition;
   heating the target using a target hotplate causing the condensation composition to form a polymerization composition, the polymerization composition having a polymerized sublimate;
   applying organic solvents to the target covered by the polymerized sublimate causing a final target surface on the target, the final target surface having a post-cleaning composition; and
   comparing the post-cleaning composition to the starting composition and concluding a cleanability of the polymerized sublimate.

2. The method of claim 1, wherein the target is a quartz disk.

3. The method of claim 1, wherein the thermal heating process is a post-apply bake process.

4. The method of claim 1, wherein the target is the same material as a chamber surface.

5. The method of claim 1, wherein the target is the same material as a wafer surface.

6. The method of claim 1, further comprising:
   placing a hot target in the chamber before the heating of the wafer, the hot target having a hot target starting composition,
   applying an organic solvent to the hot target after heating the wafer causing a final hot target surface on the hot target, the final hot target surface having a hot post-cleaning composition; and
   comparing the hot post-cleaning composition to the starting composition and concluding a cleanability of the polymerized sublimate.

7. The method of claim 6, further comprising:
   applying an organic solvent to the hot target after heating the wafer causing a final hot target surface on the hot target, the final hot target surface having a hot post-cleaning composition; and
   comparing the hot post-cleaning composition to the starting composition and concluding a cleanability of the polymerized sublimate.

8. The method of claim 1, further comprising:
   comparing the condensation composition to the starting composition and concluding an amount of sublimate outgassed from the lithography material during the heating of the wafer.

9. A method comprising:
   placing a wafer on a wafer hotplate inside a chamber with the wafer being covered by a lithography material;
   placing a target in the chamber above the wafer, wherein the target has a starting composition on a target surface thereof;
   heating the wafer using a thermal heating process, wherein the lithography material outgases a sublimate that forms a test composition on the target surface;
   applying an organic solvent to the target causing a final target surface on the target, the final target surface having a post-cleaning composition; and
   comparing the post-cleaning composition to the starting composition and concluding a cleanability of the lithography material.

10. The method of claim 9, wherein the test composition includes a solid form of the sublimate.

11. The method of claim 9, wherein the test composition includes a polymerized form of the sublimate.

12. The method of claim 9, wherein the target is a quartz disk.

13. The method of claim 9, wherein the thermal heating process is a post-apply bake process.

14. The method of claim 9, wherein the target is the same material as a chamber surface.

15. The method of claim 9, wherein the target is the same material as a wafer surface.

16. A method comprising:
    placing a target in a chamber;
    heating a material in the chamber causing a sublimate to outgas from the material and condensing on the target;
    heating the target causing the condensed sublimate to form a polymer composition, wherein the polymer composition includes a polymerized sublimate; and
    analyzing the polymerized sublimate for crosslinking.

17. The method of claim 16, wherein the target is a quartz disk.

18. The method of claim 16, further comprising:
    cleaning the target using an organic solvent after the heating the target.

19. The method of claim 18, further comprising:
    analyzing the target for a post-cleaning composition and concluding a cleanability of the polymerized sublimate.

20. The method of claim 16, further comprising:
    placing a hot target in the chamber before the heating of the material.

* * * * *